United States Patent [19]
Scaman

[11] Patent Number: 6,005,966
[45] Date of Patent: Dec. 21, 1999

[54] METHOD AND APPARATUS FOR MULTI-STREAM DETECTION OF HIGH DENSITY METALIZATION LAYERS OF MULTILAYER STRUCTURES HAVING LOW CONTRAST

[75] Inventor: Michael Edward Scaman, Peekskill, N.Y.

[73] Assignee: International Business Machines Corporation, Armonk, N.Y.

[21] Appl. No.: 08/799,517

[22] Filed: Feb. 12, 1997

[51] Int. Cl.$^6$ ..................................................... G06K 9/00
[52] U.S. Cl. .......................... 382/149; 382/171; 382/197; 382/199; 382/286
[58] Field of Search ........................... 382/145, 147–149, 382/171–173, 197, 199, 204, 218, 219, 286; 348/87, 126, 130; 356/372, 375, 376, 383, 384, 394, 237.4, 237.5; 364/468.17, 469.02; 438/16; 250/559.07, 559.08, 559.2, 559.26, 559.39, 559.42, 559.43

[56] References Cited

U.S. PATENT DOCUMENTS

| | | | |
|---|---|---|---|
| 4,162,126 | 7/1979 | Nakagawa et al. | 356/237 |
| 4,587,617 | 5/1986 | Barker et al. | 364/507 |
| 5,173,719 | 12/1992 | Taniguchi et al. | 356/394 |
| 5,177,559 | 1/1993 | Batchelder et al. | 356/237 |
| 5,355,212 | 10/1994 | Wells et al. | 356/237 |
| 5,448,650 | 9/1995 | Desai et al. | 382/141 |

OTHER PUBLICATIONS

Michael E. Scaman, Laertis Economikos, Computer Vision for Automatic Inspection of Complex Metal Patterns on Multichip Modules (MCM–D), IEEE Transactions on Components, Packaging, and Manufacturing Technology, Part B, vol. 18, No. 4, Nov. 1995, pp. 675–684.

"Computer Vision for Automatic Inspection of a High Density Grid of Pads on Multi–Chip Modules (MCM–D)", *IEEE Transactions on Componenets, Packaging, and Manufacturing Technology—Part B*, vol. 17, No. 3, pp. 291–299, Aug. 1994.

"Computer Vision for Automatic Inspection of Complex Metal Patterns on Multi–Chip Modules (MCM–D)", *IEEE Transactions on Components, Packaging, and Manufacturing Technology—Part B*, vol. 18, No. 4, pp. 1–11, Nov. 1995.

*Primary Examiner*—Leo H. Boudreau
*Assistant Examiner*—Brian P. Werner
*Attorney, Agent, or Firm*—Steven J. Soucar

[57] ABSTRACT

A method and apparatus for detecting opens and shorts in a metalization layer includes creating a reference feature list of opens features and at least two reference feature lists of shorts features included in a top surface metalization. A first of the at least two reference feature lists include shorts features having a first threshold and the second of the at least two reference feature lists include shorts features having a second threshold more aggressive than the first threshold. High numerical aperture (NA) illumination is used to produce a grey level image of the top surface metalization. A first image stream is produced from the grey level image using a first digital threshold suitable for use in detecting opens exclusive of shorts and then opens features are extracted. At least a second image stream and a third image steam are then produced from the grey level image using second and third digital thresholds, respectively, suitable for use in detecting shorts exclusive of opens. Thereafter, shorts features are extracted from the second and third image streams. Lastly, a report of extra opens features and extra shorts features extracted from the first, second, and third image streams is generated, wherein the extra opens and shorts features constitute potential flaws.

6 Claims, 5 Drawing Sheets

SMALL SHORTS
$(I_0 \geq m) \cdot (I_2 \geq \ell)$

ALT. SMALL SHORTS
$(I_0 \geq m) \cdot (I_2 \geq \ell) \cdot (I_5 < s)$

MEDIUM SHORTS
$(I_0 \geq m) \cdot (I_1 \geq \ell) \cdot (I_2 \geq m)$

ALT. MEDIUM SHORTS
$(I_0 \geq m) \cdot (I_1 \geq \ell) \cdot (I_2 \geq m) \cdot (I_5 < s)$

LARGE SHORTS $(I_1 \geq m) \cdot (I_2 \geq \ell) \cdot (I_6 \geq \ell) \cdot (I_7 \geq m)$

ALT. LARGE SHORTS $(I_1 \geq m) \cdot (I_2 \geq m) \cdot (I_5 \geq m) \cdot (I_6 \geq m)$

METHOD AND APPARATUS FOR MULTI-STREAM DETECTION OF HIGH DENSITY METALIZATION LAYERS OF MULTILAYER STRUCTURES HAVING LOW CONTRAST

BACKGROUND OF THE INVENTION

1. Field of the Invention

The present invention generally relates to the manufacture of electrical devices and, more particularly, to the automated optical inspection of metal patterns on an underlying structure or substrate.

2. Discussion of the Related Art

Fabrication of electrical and electronic devices which have included a layer of metal connections formed on an underlying layer or substrate has been a well-known practice. Printed circuits are a well-known example of such structures. Integrated circuits also include similar structures but of a much smaller size. Improvements in materials technology and semiconductor metallurgy, in particular, has resulted in ever greater degrees of miniaturization, circuit complexity and feature density in electrical devices which include such conductors.

As circuit complexity has increased, sophisticated electrical and optical methods of testing for defects have been developed in order to detect defects of a scale comparable to the feature size of the connector pattern formed. Automation of these techniques has become a practical necessity due to the number of connections usually present. These automated techniques have been generally effective in detecting actual defects in the pattern.

Electrical continuity testing is often effective and efficient in discovering defects in connection patterns since a network of signal lines may be simultaneously tested. However, there are many types of defects such as shorts to the same node and thin areas of a conductive pattern which cannot be easily detected by electrical testing. Further, the cost and complexity of some circuit modules currently being manufactured makes it economically desirable to repair defective circuits when a defect is discovered and electrical continuity testing rapidly becomes arduous if used to locate the defect for repair. For this reason, optical testing to compare a manufactured connection pattern with an intended pattern has been developed and successfully used to locate actual circuit defects. It should be noted that the location of defects may also be useful in the modification of conductor pattern designs in the manufacturing of devices which are of a scale at which repair is not, in fact, feasible. Since the optical scanning and comparison of an actual pattern with a desired pattern does not vary in procedure with the connection pattern formed, optical testing becomes economically advantageous as pattern complexity increases.

It is to be understood that optical testing equipment is commercially available to automate the testing process. Such equipment is capable of detecting variations in optically sensed patterns of a size sufficient to test patterns with any minimum feature size currently being produced and capable of detecting the shape of a variation from a desired pattern in any orientation in an automated manner. However, due to the similarity of dimension of acceptable manufacturing variation to variations in sensed patterns caused by defects, such equipment tends to reject some good patterns while passing some containing defects. Both types of errors tend to increase the cost of the circuits produced and reduce the efficiency of the manufacturing process.

The illumination used in optical testing of surface patterns include so-called dark field and bright field illumination techniques used either separately or together and at different spectral frequencies in the optical testing of circuit connection patterns. Bright field illumination is very sensitive to variations in surface topology and results in many imaging artifacts representing acceptable variations in topology and which may cause difficulty in analysis of images and many false defect detections. On the other hand, dark field illumination is problematic, in that, image contrast would generally be low, leading to a low signal to noise ratio of a reflected image of an optically scanned circuit connection pattern. In the latter instance, the circuit connection pattern may also not be easily discernable from any underlying layers.

Several different forms of image analysis are typically used in a battery of tests to determine if a connection pattern which has been produced is of acceptable quality and free from defects. However, the discovery of defects at low rates of false detection and undetected faults has been particularly difficult to achieve since many defects yield images similar to those produced as portions of a correctly formed desired pattern.

In addition to the above discussion, high density multilayer thin film structures, such as multilayer chip modules (MCMs), may include a number of high density patterned layers (e.g., 50–70 layers). For purposes of discussion, high density shall refer to patterned wiring layers in which a spacing between adjacent wires (i.e., lines), a line width, and the height on a line are all about on the same order. The layers of the MCMs may include thin film wiring layers which run predominately in the horizontal and/or vertical direction. Examples of such layers include xyz layers which may further be sandwiched between thin film mesh type voltage planes. Such MCMs are prone to significant yield losses due to shorts and opens, if the defects are not repaired early enough in a manufacturing process thereof. Electrical test is typically limited in detecting electrical defects until such time as the MCM is completely manufactured, at which time, a repair might be too late. Manual inspection may also be limited because the MCMs may be exceedingly complex and dense. The MCMs furthermore typically include a non-planar and significant topology. Remnants of underlying layers can be seen through intermediate layers, such as polyimides, which may make manual visual inspection very ineffective and problematic. In addition, the significant topology of the part being inspected and images from underlying layers, likewise, make it difficult to automatically inspect such MCMs. While most inspection techniques utilize bright illumination and require that the part being inspected be planar, the same inspection techniques are typically ineffective for inspection for opens and shorts of a wiring pattern on a MCM because of the low contrast image of the patterned metalization layer on the MCM.

Feature extraction optical inspection testing techniques are known in the art. For instance, a particular list of features can be used during an inspection, wherein the features may include line ends, junctions, or some other particular feature. The feature list may typically includes an x-y coordinate and the type of feature at the corresponding x-y coordinate. During processing of a feature extraction optical inspection, a report list is generated which typically reports all extra features and all missing features. However, for a low contrast image inspection (for example, MCM part inspection), such an optical inspection technique is highly susceptible to errors when the image of the pattern being inspected fades away. Furthermore, in the instance of low contrast images, the distinction between metal and not-metal is not easily discernable.

An example of MCM substrates having low contrast layers include complex dense x and y signal layers of an MCM substrate. The MCM substrates of this type present a screening problem as a result of excessive topology, in addition to, the thinness of an underlying intermediate polyimide layer. Such an MCM substrate is highly susceptible to the occurrence of defect coupling, i.e., the detecting of shorts and overflowing on opens and vice versa. It would thus be desirable to provide an effective method for screening of dense thin film signal layers of MCM substrates for shorts, opens, near shorts, and near opens with minimal defect coupling.

SUMMARY OF THE INVENTION

It is therefore an object of the present invention to provide a method and apparatus which can sense variations in an optically sensed pattern and reliably distinguish actual defects from acceptable manufacturing variations in the sensed pattern.

In is a further object of the invention to provide a technique and apparatus for feature extraction which is applicable to images obtained with low field illumination and which has the property of producing a minimum number of false detections and escapes (i.e., undetected defects).

In order to accomplish these and other objects of the invention, an optical inspection method and apparatus for detecting opens and shorts in a metalization layer patterned upon a top surface of a multilayer thin film structure include the following, wherein the top surface has a varied topology with low image contrast. A reference feature list of opens features and at least two reference feature lists of shorts features included in the top surface metalization is created. A first of the at least two reference feature lists includes shorts features having a first threshold and the second of the at least two reference feature lists includes shorts features having a second threshold more aggressive than the first threshold. The top surface metalization is illuminated with high numerical aperture (NA) illumination and a grey level image of the top surface metalization is generated. A first image stream is then produced from the grey level image using a first digital threshold suitable for use in detecting opens exclusive of shorts. Opens features exclusive of shorts features are then extracted from the first image stream. At least a second image stream and a third image steam are then produced from the grey level image using second and third digital thresholds, respectively, suitable for use in detecting shorts exclusive of opens. Thereafter, shorts features exclusive of opens features are extracted from the second and third image streams. Lastly, a report of extra opens features and extra shorts features extracted from the first, second, and third image streams is generated in comparison with the first, second, and third reference feature lists, respectively. The extra opens features and extra shorts features constitute potential flaws.

BRIEF DESCRIPTION OF THE DRAWINGS

The foregoing and other teachings and advantages of the present invention will become more apparent upon a detailed description of the best mode for carrying out the invention as rendered below. In the description to follow, reference will be made to the accompanying drawings, where like reference numerals are used to identify like parts in the various views and in which.

DETAILED DESCRIPTION OF A PREFERRED EMBODIMENT OF THE INVENTION

Several types of illumination are known in the art for optical imaging. So-called dark field illumination involves illumination of the field (e.g., the surface to be inspected) at a shallow angle to produce shadows which are observed and analyzed. As an alternative, so-called bright field illumination in which both collimated illumination and sensing of reflected light is done at an angle near normal to the imaged surface yields a more detailed image of small angular variations in topology. The present invention utilizes dark field illumination. In addition, an illumination wavelength is chosen to maximize contrast of the conductors with a polyimide substrate, polyimide being commonly used in the so-called distribution layers of multi-layer ceramic (MLC) structures (e.g., on the order of 425 to 525 nm).

Figure 1:
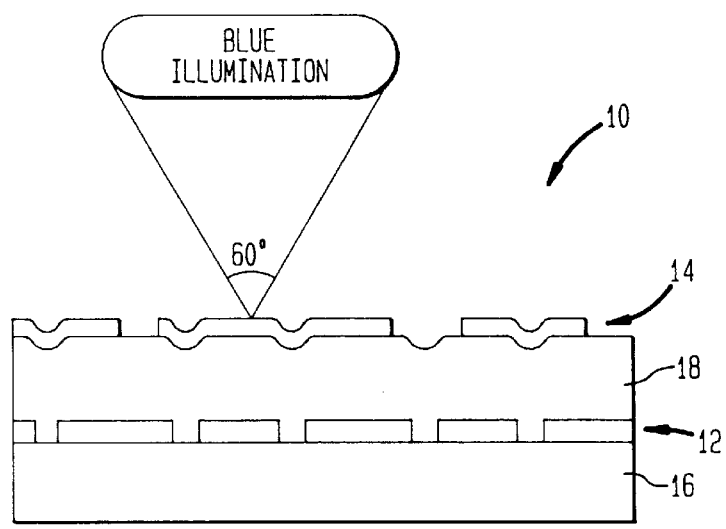
FIG. 1 shows a cross-sectional view of an MCM substrate having first and second metalization layers thereon.
Figure 2:
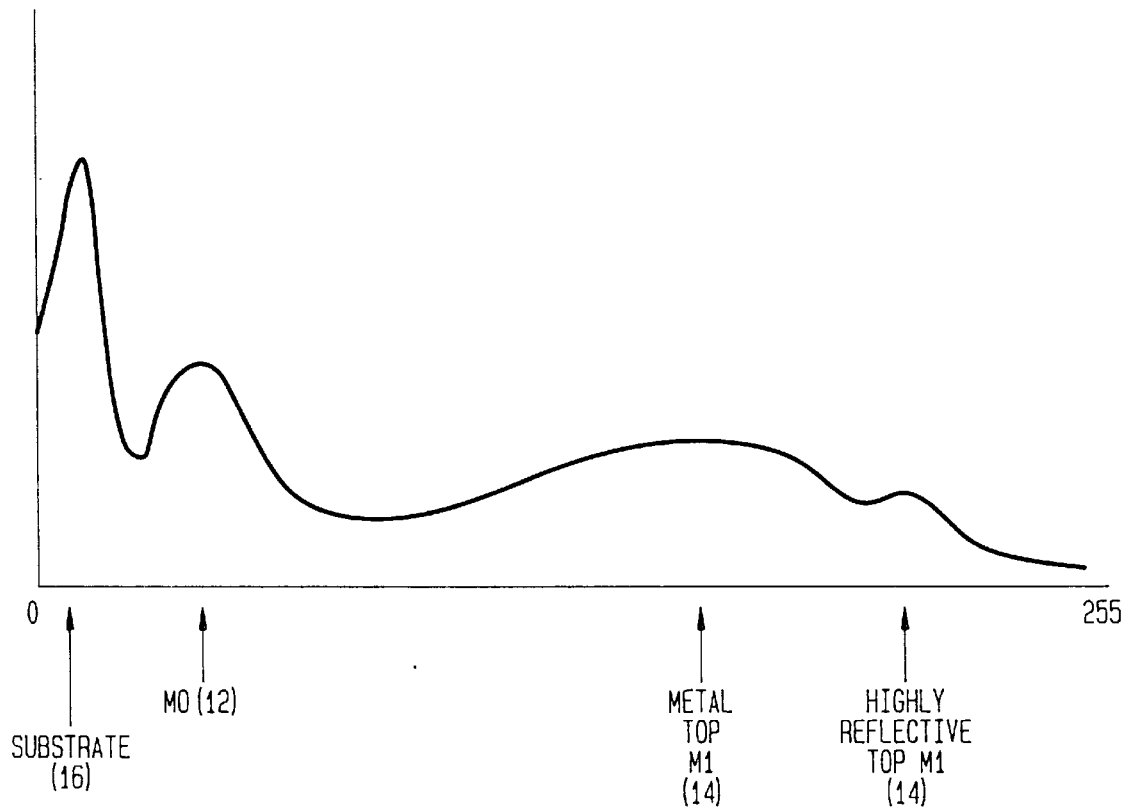
FIG. 2 exemplifies a grey level histogram of an MCM substrate such as shown in FIG. 1.

The present invention is utilized for the screening of complex dense x and y signal layers of an MCM substrate. Referring now to FIG. 1, an MCM substrate 10 having first and second metalization layers, 12 and 14, respectively, is shown. First metalization layer 12 is patterned upon a substrate 16. An intermediate layer 18 of polyimide is deposited by known techniques upon the first metalization layer 12 and substrate 16. Typical thicknesses of each respective layer of substrate 10 may include, for example, the following: polyimide layer 18 has a thickness on the order of 6 microns, and metalization layers 12 and 14 each have a thickness on the order of 6 microns. Typical line width and spacing is on the order of 10 microns. A top surface of polyimide layer 18 will contain a certain amount of varying topology as a result of the underlying metalization layer 12. A second metalization layer 14 is formed upon the top surface of polyimide layer 18. The second metalization layer 14 will be non-planar and include a topology which is influenced by the topology of the polyimide layer 18. As more and more layers are formed upon the MCM substrate 10, it is easy to understand how the topology can become extremely varying. In view of an excessive topology and the thinness of an underlying intermediate polyimide layer, it is highly unlikely to be able to have a single threshold that is sufficient for detecting shorts without overflowing on opens and vice versa. FIG. 2 exemplifies a grey level histogram of the MCM substrate 10 of FIG. 1. As shown in FIG. 2, from the grey level histogram, the top surface metal of metalization 14 does not produce a well-defined single peak. Furthermore, for an optical defect inspection technique, it is important to be able to distinguish the metalization layer 14 from the underlying metalization layer 12 and substrate 16. In accordance with the present invention, tremendous defect coupling is advantageously avoided using a multi-stream approach of defect detection. Such a multi-stream approach is used to effectively screen the MCM substrates for shorts, opens, near shorts, and near opens with a measure of success.

The present invention is distinct over known methods of defect detection. For example, the method and apparatus of the present invention does not rely heavily upon a curvature detection for shorts. Furthermore, the present invention does not require a high signal to noise image for effectiveness.

The method in accordance with the present invention is unique in that it allows for: 1) a calibration methodology for multilayer thin film inspection using a flat calibration part while the part under inspection includes a non-planar top surface; 2) a method of inspecting low contrast images including an approach to shorts detection employing progressively more aggressive thresholds for finding small, medium, and large shorts, thereby allowing a detection of high contrast small shorts, low contrast medium shorts, and low contrast large shorts (including, possible copper colored features or stains which are not easily visible with the blue light necessary to ignore underlying layers); and 3) a method of reference creation and opens detection appropriate to long signal lines which allows for underlying layers to be ignored to a significant extent. As will be discussed herein below, the present invention is distinct from prior techniques in that the present invention requires no high signal to noise images.

In the method and apparatus of the present invention, the illumination used for exposing the substrate under inspection includes high NA (60 degree cone) illumination having a wavelength on the order of 425 to 525 nm (blue light). The shorter the wavelength the less the underlying layers will show through the polyimide; however, sensitivity to red or yellow metals, such as, copper or gold will also decrease. Using blue light, the inspection tool will slow down to integrate sufficient light since there is less blackbody radiation at the shorter end of the spectrum. Thus, there are tradeoffs to consider. High NA blue light is preferably used since many typical polyimides of interest are absorbing in blue. The capping metals typical of MCM substrates include metals such as cobalt, titanium or chrome, and furthermore, tend to be silver in color and contain a blue component. The gain, offset, and light levels of the illumination are optimized for achieving target levels of brightness for the top surface metalization and the brightness as seen one layer below the surface layer.

Figure 3:
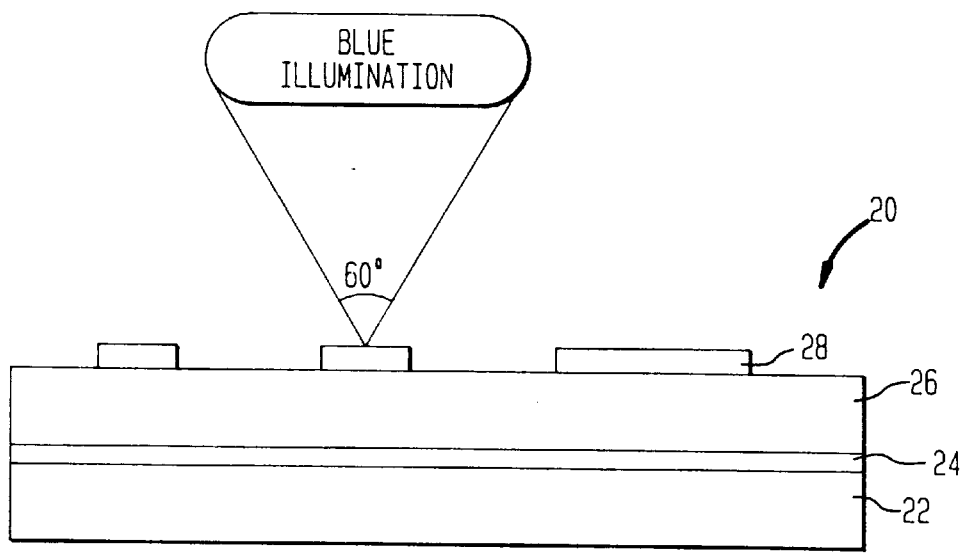
FIG. 3 shows a cross-sectional view of a flat calibration part for use in conjunction with the inspection of an MCM substrate having first and second metalization layers thereon.

In a calibration methodology of the present invention, a flat calibration part 20 as shown in FIG. 3 is used. Flat calibration part 20 includes a substrate 22 having a blanket layer of metal 24 thereon. The blanket metal layer 24 is selected to have a similar thickness and also be optically typical of the metal used one layer below the layer to be inspected of the actual part. A layer of polyimide 26 is applied to the top of metal layer 24, the polyimide having a thickness on the order typical of the intermediate polyimide layer 18 of the actual part 10 to be inspected (FIG. 1). The polyimide 26 (FIG. 3) is further characterized as having optical properties typical of the polyimide 18 of the actual part to be inspected. Lastly, a metalization pattern 28, optically typical of the top surface metalization pattern 14 of the actual part to be inspected, is provided on a top surface of polyimide layer 26. As will be discussed herein below, the same flat calibration part can be used to advantageously calibrate the inspection for successive top surface metalization layers, while ignoring metal one or more layers below.

Figure 4:
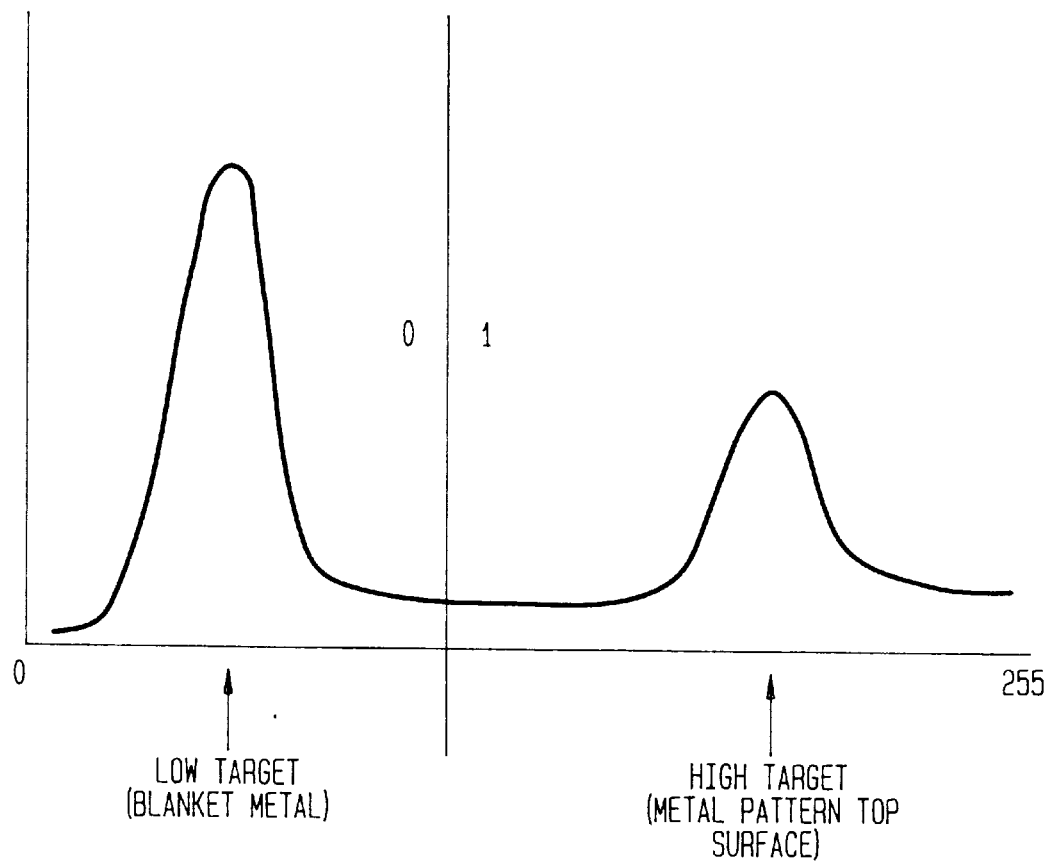
FIG. 4 exemplifies a grey level histogram of the flat calibration part such as shown in FIG. 3.

Referring now to FIG. 4, a grey level histogram of the optical front end of an optical inspection apparatus is used to iteratively test the brightness of the blanket metal 24 of the underlying layer and the surface metal of the top layer 28 (surface metalization) of the calibration part 20. Note that the present invention can be implemented using commercially available optical inspection apparatus which has been modified and programmed in accordance with the present invention, as further discussed herein. The histogram shows a grey level distribution of the pixels, wherein the darker pixels appear towards the left of the histogram and the brightest pixels appear towards the right. A peak is indicative of the brightness of a particular material distribution in the scene or field of view of the optical front end. In the present instance, a peak exists for the metal one layer below the surface (appearing on the left-hand side of the histogram) and another peak exists for the metal on the surface (appearing on the right-hand side of the histogram). As a result of the distribution having an excess of overlap between the Gaussian peaks for the left-hand and right-hand peaks, the overlap is indicative of low contrast which results in some amount of uncertainty in determining points in between peaks. The gain, offset, and light levels are iteratively adjusted and a histogram taken, until a desired target brightness of the two materials (i.e., the underlying metal layer and the surface metal) is achieved (See FIG. 4). The target brightness is a brightness selected for a particular inspection of a MCM substrate.

If the capping metal (i.e., surface metal) of each layer of the layers of the MCM substrate is the same, and if the polyimide of the respective layers is optically the same (corresponding to a same thickness and transparency), then calibrating on a single calibration part, as discussed herein above, will typically be sufficient for inspecting the top surface metalization of each layer of an MCM substrate, while ignoring metal one or more layers below. That is, the method and apparatus of the present invention advantageously include means for periodically calibrating to establish a desired target light level, gain, and offset of the illumination optical front end by adjusting the grey level peaks (i.e., one peak for the top surface metal and a second peak for metal one layer or more below) close to their expected targets. The effectiveness and meaningfulness of the inspection is thus kept at an optimum level. Calibration is further characterized by the use of the flat calibration part as shown and described with respect to FIGS. 3 and 4. Stated in another manner, calibrating the illumination to establish a desired light level, gain, and offset includes the step of effectively adjusting the imaged grey level peaks of the top surface metalization 28 and the underlying blanket metal layer 24 of the flat calibration part 20 to be close to the expected digital targets, such as shown in FIG. 4. For example, a high target peak for the top surface metalization may be expected at approximately 220 and a low target peak for the underlying blanket metal may be expected at approximately 20 on the digital axis from 0 to 255 of the gray level histogram. Calibration of the illumination with the use of the flat calibration part in this manner is highly effective in lieu of calibrating with a substrate having a top surface metalization and more than one metalization layers below the top surface metalization.

In accordance with the present invention, a reference creation and feature list methodology shall now be discussed. A set of five families of feature extraction templates are used for detecting features from a binary image. The feature extraction templates include: i) a line end feature, (ii) a space end feature, (iii) a small shorts feature, (iv) a medium shorts feature, and (v) a large shorts feature. A feature list of each layer to be inspected is necessary. Such a feature list can be made using a golden part. The feature list may likewise be made using the flat calibration part, where the pattern on the flat calibration part was made to match the pattern being inspected. Alternatively, computer aided design (CAD) data may be used, if available, for creating the necessary feature list.

In order to achieve improved defect detection capability, the present invention provides feature extraction templates, which are specified in terms of vectors emanating at angular intervals from an arbitrary point (e.g., image pixel location) on the imaged surface and determining, along those vectors, the points at which foreground image values, if any, are encountered. Foreground image values correspond, for example, to digital "1," whereas background image values correspond to digital "0." The condition of encountering or not encountering foreground information within a predetermined distance from the origin of each of the vectors of the template can then be used to determine whether the image area in the vicinity of any given image pixel location satisfies the pattern of the template. More specifically, the templates according to the invention are designed to result in positive detection when overlaying portions of the imaged pattern in a manner in order to discriminate the features of interest as discussed herein below.

Figure 5:
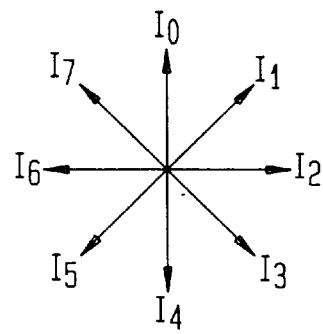
FIG. 5 is an illustration of a vector convention for the templates in accordance with the present invention.

FIG. 5 shows an array of vectors and reference numerals which will be used as a convention in the further detailed discussion of the invention, below. It is to be understood that commercial automated optical inspection tools provide for the rotation of this array of vectors and, hence, the rotation of the templates. In FIG. 5, the vectors are preferably arranged at equal angular intervals of 45° and, as a convention, numbered clock-wise from $I_0$ consecutively through $I_7$. Eight vectors are considered to be a minimum number which is currently preferred because of the rotation capabilities currently available in automated optical inspection machines. However, it is to be understood that other larger numbers of vectors at correspondingly smaller or varied angular separations could also be used.

In the instance of scanning of an actual part under inspection, the binary image of the part is scanned for the features contained in the feature list. Occurrences of extra features only are reported as potential flaws and the feature extraction templates which are used during scanning are slightly more sensitive than the ones used during reference creation. In accordance with the present invention, the feature templates are each utilized on different image streams for advantageously avoiding defect coupling. Furthermore, the features are characterized by a triple of numbers and a set of conditional expressions, to be further discussed below. A recommend list for further processing is generated utilizing the outcome of the feature list extraction on at least three separate streams of images.

In view of the extremely low contrast images which are available for a particular top surface metalization layer of the MCM substrate, it is typically not possible to detect both shorts and opens at the same time without an undesirable defect coupling. Likewise, the overkill involved in imaging of lines of the top surface metalization, in terms of false opens when you can detect shorts, or false shorts when you can detect opens, is generally substantial and thus undesirable. In accordance with the present invention, the selected feature templates are such that the opens templates will not detect false shorts and the shorts templates will not detect occurrences of false opens. The detection of opens and shorts are dealt with independently using separate image streams, each image stream having a separate digital threshold appropriate for the type of defect being templated. In other words, the digital threshold is determined by the type of template being used, in accordance with the present invention.

In a first stream, also referred to herein as the open stream, two distinct line end templates are used as follows. The two line end reference templates correspond to a line end reference template and a line end inspection template. The distinction between the two templates is in that the first template is used during reference creation and the second template is used during feature extraction of the part being inspected. In other words, a reference list of opens is created using the line end reference template. Open features are extracted from an image of the reference part using the line end inspection template. During an actual part inspection, potential open flaws are those extra features identified using the line end inspection template. Open features are extracted from an image of the actual part under inspection in which the image is converted into a digital image using a digital threshold appropriate for opens detection. With respect to the line end inspection template, however, the line end inspection template is more conservative that the line end reference template, as will be discussed further herein below.

In accordance with the present invention, the line end templates may also be either strictly horizontal or strictly vertical, or both. The line end templates do not detect diagonally running remnants, such as, possible remnants of a diagonal underlying mesh. The use of either horizontal or vertical line end templates assumes that the lines on the layer being inspected are predominately in the x-direction and y-direction. In instances where it is known that the metal lines are predominately in one direction, for example, such as the x-direction, the opens inspection may be restricted to templating horizontally for x-layers. As a result, the opens inspection is optimized.

During the creation of a list of potential opens flaws contained in the top surface metalization of the part under inspection, an appropriate binary threshold for opens is utilized for converting the analog image into a digital image. In other words, the grey level histogram of the image is used for selecting an appropriate binary threshold for use when converting the analog image data into digital data for opens detection. Utilizing the appropriate threshold renders the detection of opens robust with respect to occurrences of false shorts. The digital image of the part is then scanned in a serpentine fashion for opens using the line end inspection template. The line end inspection template is utilized for extracting occurrences of extra features.

Figure 6:
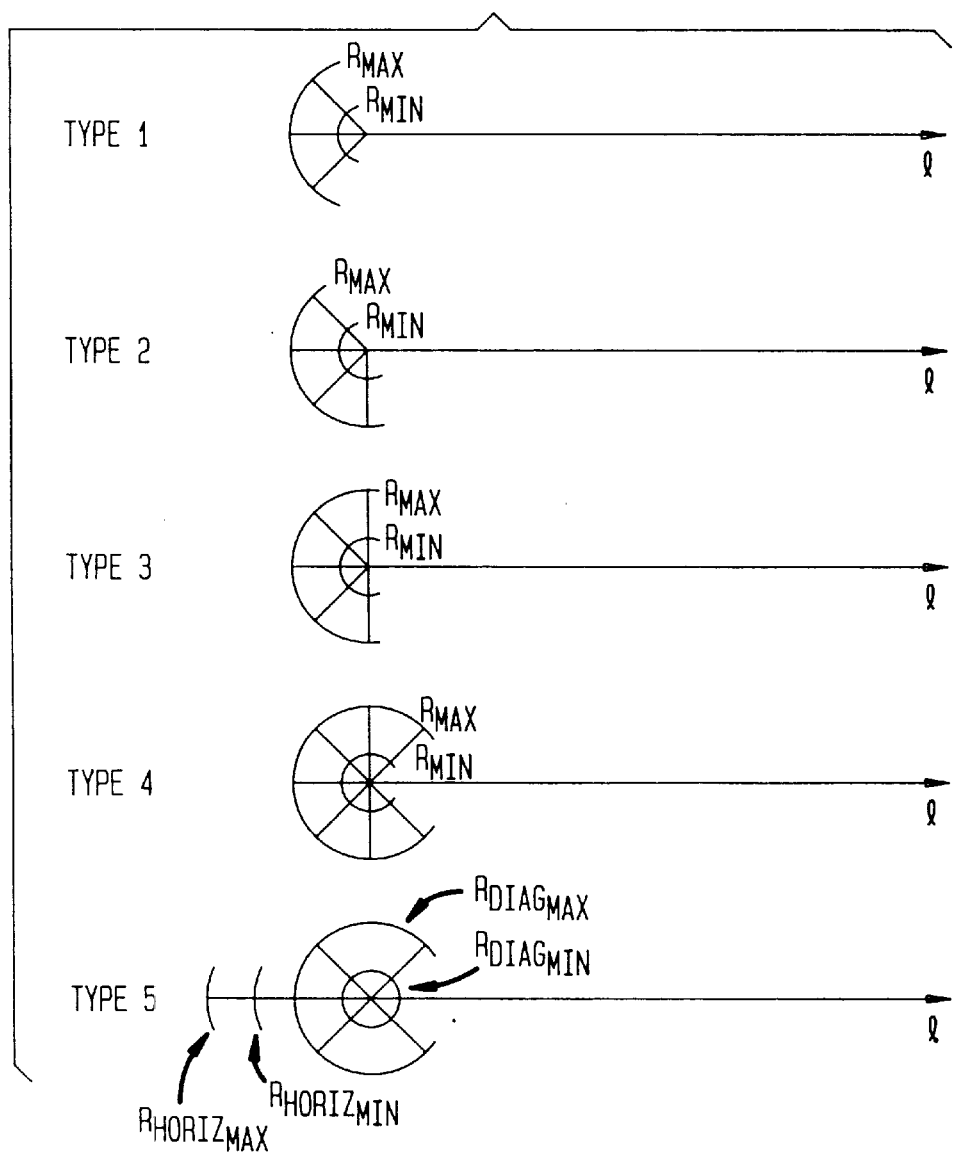
FIG. 6 illustrates the line-end feature extraction templates in accordance with the present invention.

Turning now to FIG. 6, five line end (LE) templates are shown. Type 1 LE template is characterized by the following logical expression:

$$(I_2 \geq l) \cdot (R_{MIN} < I_5 < R_{MAX}) \cdot (R_{MIN} < I_6 < R_{MAX}) \cdot (R_{MIN} < I_7 < R_{MAX}).$$

Type 2 LE template is characterized by the following logical expression:

$$(I_2 \geq l) \cdot (R_{MIN} < I_4 < R_{MAX}) \cdot (R_{MIN} < I_5 < R_{MAX}) \cdot (R_{MIN} < I_6 < R_{MAX}) \cdot (R_{MIN} < I_7 < R_{MAX}).$$

Type 3 LE template is characterized by the following logical expression:

$$(I_2 \geq l) \cdot (R_{MIN} < I_0 < R_{MAX}) \cdot (R_{MIN} < I_4 < R_{MAX}) \cdot$$
$$(R_{MIN} < I_5 < R_{MAX}) \cdot (R_{MIN} < I_6 < R_{MAX}) \cdot (R_{MIN} < I_7 < R_{MAX}).$$

Type 4 LE template is characterized by the following logical expression:

$$(I_2 > l) \cdot (R_{MIN} < I_0 < R_{MAX}) \cdot (R_{MIN} < I_1 < R_{MAX}) \cdot$$
$$(R_{MIN} < I_3 < R_{MAX}) \cdot (R_{MIN} < I_4 < R_{MAX}) \cdot$$
$$(R_{MIN} < I_5 < R_{MAX}) \cdot (R_{MIN} < I_6 < R_{MAX}) \cdot (R_{MIN} < I_7 < R_{MAX}).$$

Type 5 LE template is characterized by the following logical expression:

$$(I_2 > l) \cdot (Rdiag_{MIN} < I_1 < Rdiag_{MAX}) \cdot$$
$$(Rdiag_{MIN} < I_3 < Rdiag_{MAX}) \cdot (Rdiag_{MIN} < I_5 < Rdiag_{MAX}) \cdot$$
$$(Rdiag_{MIN} < I_7 < Rdiag_{MAX}) \cdot (Rhorz_{MIN} < I_6 < Rhorz_{MAX})$$

The Type 1 LE template is a less aggressive template than the Type 2, Type 3, Type 4, and Type 5 LE templates. In other words, the LE templates are progressively more aggressive from the Type 1 LE template to the Type 5 LE template. In addition, in regard to the difference between the reference LE template and the inspection LE template, the reference LE template is always selected to have a lower type than the inspection LE template. In the preferred implementation, the reference is learned with a Type 1, 2, 3 or 4 (preferably 3) template and inspected with a higher numbered template (preferably 5). Only extra features are recorded as potential flaws in the potential flaws list, whereas missing features are ignored.

In connection with the above discussion of the LE templates of FIG. 6, note that a line end includes a pad feature, the later of which is described by a set of triples. The set of triples correspond to a diagonal diameter (d), a horizontal/vertical diameter (h), and a tolerance (t), in accordance with a particular optical inspection operation. A line end feature is thus characterized by the set of triples, in addition to the conditional expressions based on ANDed terms of combinations of particular rays $I_{0-7}$ being within the range of $R_{MIN}$ and $R_{MAX}$, or greater than $R_{MAX}$ (i.e., "l" as shown in FIG. 6). It is possible for a ray to be greater than a prescribed hardware limit, for example, on the order of approximately 145 pixels for a long tail. Diagonal rays, corresponding to $I_1$, $I_3$, $I_5$, and $I_7$, would be subject to a diagonal minimum and maximum. Furthermore, horizontal and vertical rays, corresponding to $I_0$, $I_2$, $I_4$, and $I_6$, would be subject to a horizontal and vertical minimum and maximum. Suitable expressions for $R_{MIN}$ and $R_{MAX}$ further include:

(i) $R_{MIN}$(diagonal)=diagonal diameter−tolerance/2, (ii) $R_{MAX}$(diagonal)=diagonal diameter+tolerance/2, (iii) $R_{MIN}$(horz/vert)=horz/vert diameter−tolerance/2, and (iv) $R_{MAX}$(horz/vert)=horz/vert diameter+tolerance/2.

In practice, these values can be empirically refined, depending on the actual patterns, the processes by which the patterns are produced and the particulars of the illumination and optical sensing set-up being used.

Figure 7:
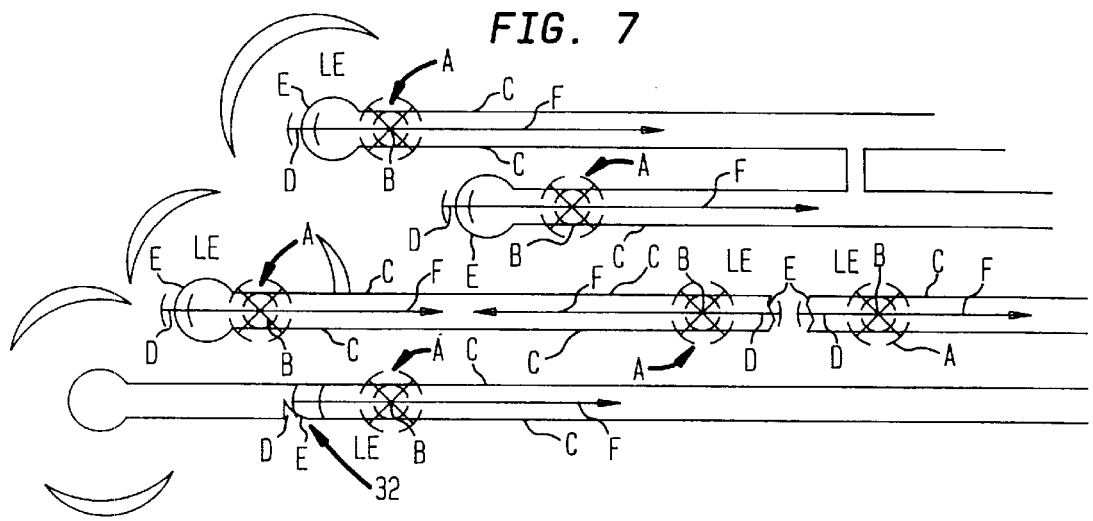
FIG. 7 illustrates an application of the line-end feature extraction templates to an MCM substrate under inspection.

During the opens stream, the particular selected LE inspection template is used for opens detection. The horizontally and/or vertically applied LE inspection template will detect an open, such as indicated by numeral 30 of FIG. 7, by the occurrence of an extra feature while being tolerant to small shorts. The LE inspection template may even detect near opens such as indicated by numeral 32 of FIG. 7. The diagonal lines A indicate that the point B satisfies the range of diagonal distance to the edge C in these directions. The short horizontal line D indicates that the point B satisfies the range of horizontal distance to the edge E in that direction. The long horizontal line F indicates that the point B satisfies the requirement of seeing no edge (not shown) within l (a set number) of pixels in that direction, i.e., the long horizontal line is continuous for l pixels.

In a second stream, also referred to herein as the smallest shorts class stream, a threshold appropriate for producing a binary image with minimal occurrences of false shorts is appropriately selected. The resulting binary image created using the selected smallest shorts threshold is then used for feature extraction inspection of the smallest-thinnest class of shorts defects. While false opens may occur using the smallest shorts binary threshold, the smallest shorts feature extraction template is insensitive to such false opens. For explanation purposes, false opens result in the situation wherein a short actually exists but gets falsely identified as an open.

With reference to the smallest shorts class stream, a dead end space template is utilized for feature extraction of the smallest shorts. Using the same methodology as for opens detection, an inverse of the image is used for detection of dead end spaces, since a short between two parallel lines will typically result in a type of dead end. Similarly as with the opens detection, a reference smallest shorts class feature list is built using a reference line end type and the digital image of the part under inspection is scanned using the inspection line end type. In both instances, the template is applied to the binary inverse of the segmented digital image.

Figure 8A:
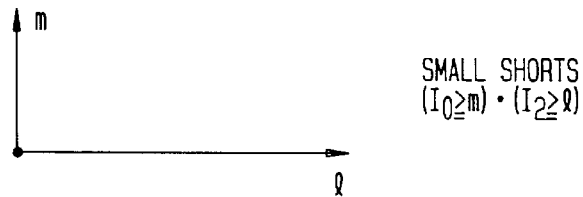
FIGS. 8A and 8B illustrate the small shorts feature extraction templates in accordance with the present invention.
Figure 8B:
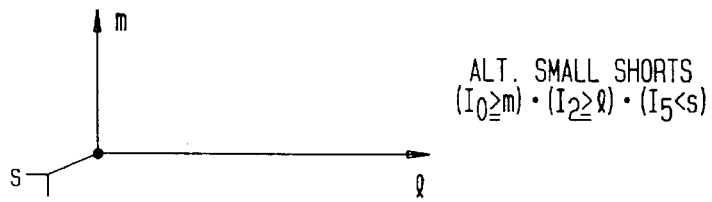

With reference to the smallest shorts class stream, also referred to herein as the small shorts class stream, the threshold appropriate for producing a binary image with minimal occurrences of false shorts is appropriately selected. With reference to the small shorts class stream, a small shorts template is utilized for feature extraction of the small shorts. The small shorts template is characterized as having a "T" or "L" shape. A golden reference feature list of all bends and junctions on the part under inspection is made, as appropriate. The golden reference feature list is used in conjunction with the small shorts template for identifying extra occurrences of small shorts features, which may indicate a defect (i.e., a undesired short). The small shorts template is further characterized by the following logical expression: $(I_0 \geq m) \cdot (I_2 \geq l)$ as shown in FIG. 8A. If the part under inspection is includes large areas of extra metal, giving rise to potential gross shortings, the small shorts template can be modified in the fashion as shown in FIG. 8B. The modified small shorts template is characterized by the logical expression: $(I_0 \geq m) \cdot (I_2 \geq l) \cdot (I_5 < s)$. As modified, the small shorts template helps prevent the inspection tool from choking on excessive detection clouds of areas of large metal on the top surface of the part under inspection.

Figure 9A:
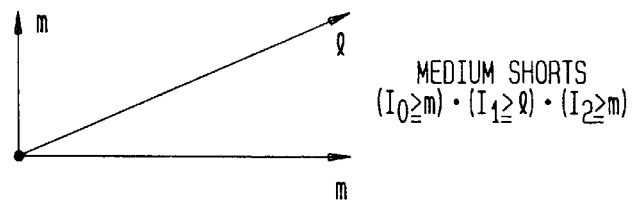
FIGS. 9A and 9B illustrate the medium shorts feature extraction templates in accordance with the present invention.
Figure 9B:
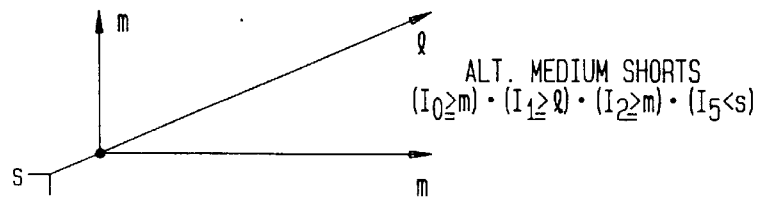

In a third stream, also referred to herein as the medium shorts class stream, the threshold appropriate for producing a binary image with more aggressive occurrences of very small false shorts is selected. With reference to the medium shorts class stream, a medium shorts template is utilized for feature extraction of the medium shorts, that is, the next largest class of shorts. It is assumed that the product under inspection includes primarily only lines of a certain thickness and by design no areas will have lines twice that size or larger. The medium shorts template is selected to detect areas of metal where lines bulge sufficiently. In general, the medium shorts template will detect areas of about two times (2×) the line width of extra metal or greater. The medium shorts template is insensitive to small islands of metal and areas of metal having typical line widths. As a result, the medium shorts inspection stream will be tolerant to opens, as well as very small shorts. The medium shorts template is characterized by the logical expression: $(I_0 \geq m) \cdot (I_1 \geq l) \cdot (I_2 \geq m)$, as shown in FIG. 9A. If the part under inspection is includes large areas of extra metal, giving rise to potential gross shortings, the medium shorts template can be restricted and modified in the fashion as shown in FIG. 9B. That is, the modified medium shorts template is characterized by the logical expression: $(I_0 \geq m) \cdot (I_1 \geq l) \cdot (I_2 \geq m) \cdot (I_5 < s)$. As modified, the medium shorts template helps prevent the inspection tool from choking on excessive detection clouds of areas of large metal on the top surface of the part under inspection.

Figure 10A:
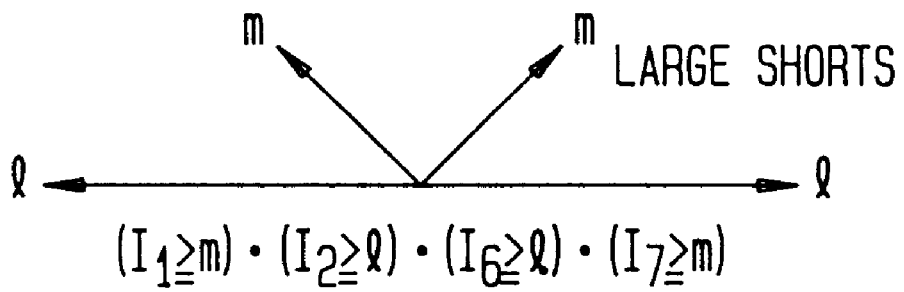
FIGS. 10A and 10B illustrate the large shorts feature extraction templates in accordance with the present invention.
Figure 10B:
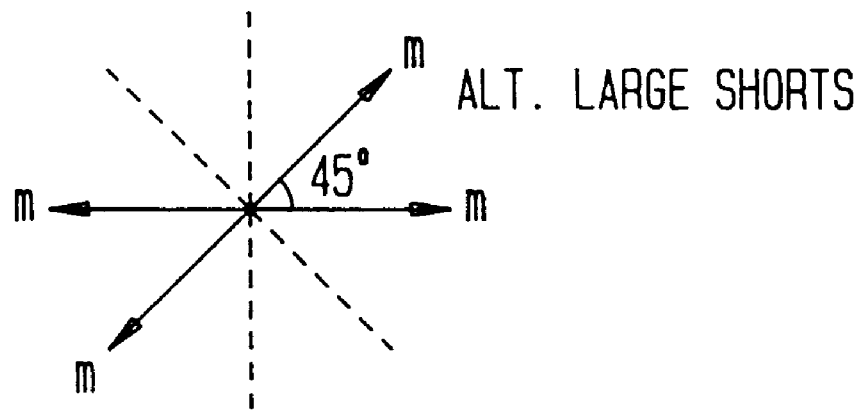

In a fourth stream, also referred to herein as the low contrast large shorts class stream, a threshold appropriate for producing a binary image with more aggressive shorts detection is selected for detecting the occurrences of large shorts, including possibly low contrast large shorts. A large low contrast short may include a conductive haze, for example. This latest threshold shall be used when inspecting for the largest class of shorts. The aggressive large shorts detection threshold is tolerant to both small and medium shorts, but detects larger shorts and/or low contrast areas of bulged lines. The aggressive large shorts detection threshold is also tolerant of areas of false opens. With reference to the large shorts stream, it is assumed that the product being inspected includes only lines of a certain thickness and by design no areas will have lines twice that size or larger. A large shorts template is utilized for feature extraction of the large shorts. The large shorts template is characterized by the following logical expression: $(I_1 \geq m) \cdot (I_2 \geq l) \cdot (I_6 \geq l) \cdot (I_7 \geq m)$, as shown in FIG. 10A. The large shorts template, as described, will detect areas of bulged lines and areas of shorting metal on the order of about four times (4×) the line width. Alternatively, the large shorts template can be modified in the fashion as shown in FIG. 10B. The modified large shorts template is characterized by the following logical expression: $(I_1 \geq m) \cdot (I_2 \geq m) \cdot (I_5 \geq m) \cdot (I_6 \geq m)$. As modified, the large shorts template helps prevent the inspection tool from choking on excessive detection clouds of areas of large metal on the top surface of the part under inspection.

Upon completion of the feature extractions of the first stream and at least two of the second through fourth streams, all cases of extra features are reviewed on a verification station which includes an x-y stage (not shown). All defects (i.e., extra features) are classified for repair or possibly to scrap the part. In accordance with the present invention, only extra features are selected during feature extraction. If the part under inspection is a multi-up substrate, such as, a 2 by 2 substrate, flaws on chicklettes (i.e., one quarter of the 2 by 2 substrate) which have been previously scrapped will be discarded. Other substrates may include 4-up, 16-up, 25-up, etc., where X-up corresponds to the building of X layouts at the same time on a single laminate.

The junction feature templates used in accordance with the present invention include one or more arrows to indicate an existence of a foreground feature greater than a particular distance of m or l. A reversed arrow or forked end of a vector is used to indicate that an existence of a foreground edge encountered within a distance s. It may be useful to observe that s, m and l are used to indicate relative distance magnitudes of small, medium and large, respectively. Of course, it is to be understood that the values of s, m and l could be changed in consideration of particular pattern characteristics. Thus, the conditional expressions contained in the respective templates, amount to saying that an edge must be within s pixels, or an edge must be further away than m or l pixels, as appropriate. The junction features are thus described by a set of triples of s, m, and l in addition to the conditional expressions based on ANDed terms of combinations of particular rays $I_{0-7}$ being less than s, greater than m, and greater than l.

When it is considered that each of s, m and l are particular distances along each respective vector and can thus be easily translated into particular coordinates, it is clear that these expressions represent combinations of go/no go tests which may be rapidly performed. Since the terms of the expressions are logically ANDed, a violation is simply a comparison of coordinates corresponding to distances s, m and l from the origin or pixel location and the digital threshold converted image data. Any failure of the defined conditions can be easily detected as assigned to each vector at each rotation of a template. The potential defects, noted as extra features, are thus identified and later evaluated to determine whether or not a defect, in fact, exists and whether or not corrective action should be taken.

Nominal values of s, m and l are set as s=2×nominal minimum feature size (e.g., line width), m<line pitch (e.g., minimum line spacing on centers) and l≈1.414×m. In practice, these values can often be empirically refined, depending on the actual patterns, the processes by which the patterns are produced and the particulars of the illumination and optical sensing set-up being used. The present invention can be used in conjunction with other statistical, optical or feature extraction techniques to further improve performance such as establishing a "don't care" zone along the edges of certain types of connection lines (e.g., the heavy gold lines) to reduce image artifact density.

Also, it should be noted that the templates in accordance with the invention assist in the speed of operation of commercially available optical testing tools since the symmetry of some templates eliminate a substantial number of rotations which must be tested. Further, since all templates may be described in terms of ANDed conditions, only one violation of the template conditions need be found for a possible detection to be rejected.

As noted above, the technique of the present invention is particularly effective for extremely dense x-y wiring layers or portions of x-y wiring layers of the image pattern. Accordingly, the throughput of the process in accordance with the present invention could be increased by limiting its application to such areas. Whether or not such limitation is done, merger of the data obtained by the technique in accordance with the present invention can be merged with defect data derived through other optical or electrical techniques which may have similar preferential applicability to optimize overall defect detection accuracy and throughput rates.

There has thus been shown a method and apparatus which provides feature extraction applicable to images obtained with low field illumination (i.e., low image contrast) and producing a minimum number of false detections and escapes.

While the invention has bee particularly shown and described with reference to specific embodiments thereof, it will be understood by those skilled in the art that various changes in form and detail may be made thereto, and that other embodiments of the present invention beyond embodiments specifically described herein may be made or practice without departing from the spirit of the invention. Similarly, other changes, combinations and modifications of the presently disclosed embodiments will also become apparent. The embodiments disclosed and the details thereof are intended to teach the practice of the invention and are intended to be illustrative and not limiting. Accordingly, such apparent but undisclosed embodiments, changes, combinations, and modifications are considered to be within the spirit and scope of the present invention as limited solely by the appended claims.

What is claimed is:

1. A method of detecting opens and shorts in a metalization layer patterned upon a top surface of a multilayer thin film structure, the top surface having a varied topology with low image contrast, said method comprising the steps of:

creating a reference feature list of opens features included in the top surface metalization, the reference feature list including opens having a first threshold;

creating at least two reference feature lists of shorts features included in the top surface metalization, a first of the at least two reference feature lists including shorts features having a second threshold and the second of the at least two reference feature lists including shorts features having a third threshold more aggressive in the detection of larger shorts than the first threshold and wherein creating a reference feature list of opens features includes utilizing a line end reference template, and creating at least two reference feature lists of shorts features includes utilizing at least two templates selected from the following group consisting of smallest shorts template, small shorts template, medium shorts template, and large shorts template;

illuminating the top surface metalization with high numerical aperture (NA) illumination and generating a grey level image of the top surface metalization;

producing a first image stream from the grey level image using said first digital threshold suitable for use in detecting opens exclusive of shorts and extracting opens features exclusive of shorts features from the first image stream;

producing at least a second image stream and a third image steam from the grey level image using said second and third digital thresholds, respectively, suitable for detecting shorts exclusive of opens and extracting shorts features exclusive of opens features from the second and third image streams; and generating a report of extra opens features and extra shorts features extracted from the first, second, and third image streams in comparison with the first, second, and third reference feature lists, respectively, wherein the extra opens features and extra shorts features constitute potential flaws.

2. A method of detecting opens and shorts in a metalization layer patterned upon a top surface of a multilayer thin film structure, the top surface having a varied topology with low image contrast, said method comprising the steps of:

creating a reference feature list of opens features included in the top surface metalization, the reference feature list including opens having a first threshold;

creating at least two reference feature lists of shorts features included in the top surface metalization, a first of the at least two reference feature lists including shorts features having a second threshold and the second of the at least two reference feature lists including shorts features having a third threshold more aggressive in the detection of larger shorts than the first threshold;

illuminating the ton surface metalization with high numerical aperture (NA) illumination and generating a grey level image of the top surface metalization;

producing a first image stream from the grey level image using said first digital threshold suitable for use in detecting opens exclusive of shorts and extracting opens features exclusive of shorts features from the first image stream;

producing at least a second image stream and a third image steam from the grey level image using said second and third digital thresholds, respectively, suitable for detecting shorts exclusive of opens and extracting shorts features exclusive of opens features from the second and third image streams; and wherein extracting opens features from the first image stream includes utilizing a line end inspection template, and extracting shorts features from the second and third image streams includes utilizing at least two different shorts templates, further wherein a respective shorts template is selected from the group consisting of a smallest shorts template, a small shorts template, a medium shorts template, and a large shorts template for extracting shorts consisting of smallest shorts, small shorts, medium shorts, and large shorts, respectively; and generating a report of extra opens features and extra shorts features extracted from the first, second, and third image streams in comparison with the first, second, and third reference feature lists, respectively, wherein the extra opens features and extra shorts features constitute potential flaws.

3. A method of detecting opens and shorts in a metalization layer patterned upon a top surface of a multilayer thin film structure, the top surface having a varied topology with low image contrast, said method comprising the steps of:

creating a reference feature list of opens features included in the top surface metalization, the reference feature list including opens having a first threshold;

creating at least two reference feature lists of shorts features included in the top surface metalization, a first of the at least two reference feature lists including shorts features having a second threshold and the second of the at least two reference feature lists including shorts features having a third threshold more aggressive in the detection of larger shorts than the first threshold;

illuminating the top surface metalization with high numerical aperture (NA) illumination and generating a grey level image of the top surface metalization;

calibrating the illumination to establish a desired light level, gain, and offset, said calibration step including the step of adjusting imaged grey level peaks of a top surface metalization and an underlying blanket metal layer, respectively, of a flat calibration part to be close to expected digital targets, wherein said calibration step is effective for use in lieu of calibrating with a substrate having a top surface metalization and more than one metalization layers below the top surface metalization;

producing a first image stream from the grey level image using said first digital threshold suitable for use in detecting opens exclusive of shorts and extracting opens features exclusive of shorts features from the first image stream;

producing at least a second image stream and a third image steam from the grey level image using said second and third digital thresholds, respectively, suitable for detecting shorts exclusive of opens and extracting shorts features exclusive of opens features from the second and third image streams; and generating a report of extra opens features and extra shorts features extracted from the first, second, and third image streams in comparison with the first, second, and third reference feature lists, respectively, wherein the extra opens features and extra shorts features constitute potential flaws.

4. An optical inspection apparatus for detecting opens and shorts in a metalization layer patterned upon a top surface of a multilayer thin film structure, the top surface having a varied topology with low image contrast, said apparatus comprising:

means for creating a reference feature list of opens features included in the top surface metalization, the reference feature list including opens having a first threshold;

means for creating at least two reference feature lists of shorts features included in the top surface metalization, a first of the at least two reference feature lists including shorts features having a second threshold and the second of the at least two reference feature lists including shorts features having a third threshold more aggressive in the detection of larger shorts than the first threshold;

wherein said means for creating a reference feature list of opens features includes a line end reference template, and said means for creating at least two reference feature lists of shorts features includes at least two templates selected from the following group consisting of smallest shorts template, small shorts template, medium shorts template, and large shorts template;

means for illuminating the top surface metalization with high numerical aperture (NA) illumination and generating a grey level image of the top surface metalization;

means for producing a first image stream from the grey level image using said first digital threshold suitable for use in detecting opens exclusive of shorts and extracting opens features exclusive of shorts features from the first image stream;

means for producing at least a second image stream and a third image steam from the grey level image using said second and third digital thresholds, respectively, suitable for detecting shorts exclusive of opens and extracting shorts features exclusive of opens features from the second and third image streams; and means for generating a report of extra opens features and extra shorts features extracted from the first, second, and third image streams in comparison with the first, second, and third reference feature lists, respectively, wherein the extra opens features and extra shorts features constitute potential flaws.

5. An optical inspection apparatus for detecting opens and shorts in a metalization layer patterned upon a top surface of a multilayer thin film structure, the top surface having a varied topology with low image contrast, said apparatus comprising:

means for creating a reference feature list of opens features included in the top surface metalization, the reference feature list including opens having a first threshold;

means for creating at least two reference feature lists of shorts features included in the top surface metalization, a first of the at least two reference feature lists including shorts features having a second threshold and the second of the at least two reference feature lists including shorts features having a third threshold more aggressive in the detection of larger shorts than the first threshold;

means for illuminating the top surface metalization with high numerical aperture (NA) illumination and generating a grey level image of the top surface metalization;

means for producing a first image stream from the grey level image using said first digital threshold suitable for use in detecting opens exclusive of shorts and extracting opens features exclusive of shorts features from the first image stream;

means for producing at least a second image stream and a third image steam from the grey level image using said second and third digital thresholds, respectively, suitable for detecting shorts exclusive of opens and extracting shorts features exclusive of opens features from the second and third image streams; wherein said means for extracting opens features from the first image stream includes a line end inspection template, and said means for extracting shorts features from the second and third image streams includes at least two different shorts templates, further wherein a respective shorts template is selected from the group consisting of a smallest shorts template, a small shorts template, a medium shorts template, and a large shorts template for extracting shorts consisting of smallest shorts, small shorts, medium shorts, and large shorts, respectively; and means for generating a report of extra opens features and extra shorts features extracted from the first, second, and third image streams in comparison with the first, second, and third reference feature lists, respectively, wherein the extra opens features and extra shorts features constitute potential flaws.

6. An optical inspection apparatus for detecting opens and shorts in a metalization layer patterned upon a top surface of a multilayer thin film structure, the top surface having a varied topology with low image contrast, said apparatus comprising:

means for creating a reference feature list of opens features included in the top surface metalization, the reference feature list including opens having a first threshold;

means for creating at least two reference feature lists of shorts features included in the top surface metalization, a first of the at least two reference feature lists including shorts features having a second threshold and the second of the at least two reference feature lists including shorts features having a third threshold more aggressive in the detection of larger shorts than the first threshold;

means for illuminating the top surface metalization with high numerical aperture (NA) illumination and generating a grey level image of the top surface metalization;

means for calibrating the illumination means to establish a desired light level, gain, and offset, said calibration means including means for adjusting imaged grey level peaks of a top surface metalization and an underlying blanket metal layer, respectively, of a flat calibration part to be close to expected digital targets, wherein said calibration means is effective for use in lieu of calibrating with a substrate having a top surface metalization and more than one metalization layers below the top surface metalization;

means for producing a first image stream from the grey level image using said first digital threshold suitable for use in detecting opens exclusive of shorts and extracting opens features exclusive of shorts features from the first image stream:

means for producing at least a second image stream and a third image steam from the grey level image using said second and third digital thresholds, respectively, suitable for detecting shorts exclusive of opens and extracting shorts features exclusive of opens features from the second and third image streams; and means for generating a report of extra opens features and extra shorts features extracted from the first, second, and third image streams in comparison with the first, second, and third reference feature lists, respectively, wherein the extra opens features and extra shorts features constitute potential flaws.

* * * * *